(12) United States Patent
Salem et al.

(10) Patent No.: US 7,344,887 B2
(45) Date of Patent: Mar. 18, 2008

(54) METHODS AND PRODUCTS FOR DELIVERING BIOLOGICAL MOLECULES TO CELLS USING MULTICOMPONENT NANOSTRUCTURES

(75) Inventors: Aliasger Karimjee Salem, Coralville, IA (US); Kam W. Leong, Ellicott City, MD (US); Peter Charles Searson, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 328 days.

(21) Appl. No.: 10/875,543

(22) Filed: Jun. 24, 2004

(65) Prior Publication Data
US 2005/0101020 A1    May 12, 2005

Related U.S. Application Data

(60) Provisional application No. 60/482,141, filed on Jun. 24, 2003.

(51) Int. Cl.
C12N 15/64 (2006.01)

(52) U.S. Cl. .................. 435/459; 435/470; 435/471; 514/44

(58) Field of Classification Search .................. None
See application file for complete search history.

(56) References Cited

U.S. PATENT DOCUMENTS

| 5,460,831 A | 10/1995 | Kossovsky et al. ......... 424/493 |
| 5,578,325 A | 11/1996 | Domb et al. ................ 424/501 |
| 6,048,515 A | 4/2000 | Kresse et al. ............ 424/9.322 |
| 6,475,995 B1 | 11/2002 | Roy et al. ..................... 514/44 |

FOREIGN PATENT DOCUMENTS

WO    WO03/051278    6/2003

OTHER PUBLICATIONS

Nicewarner-Pena, Sheila R. et al., "Submicrometer Metallic Barcodes", Science Oct. 5, 2001, vol. 294, pp. 137-141.
Martin, Charles R., "Nanomaterials: A Membrane-Based Synthetic Approach", Science, New Series, vol. 266, Issue 5193 (Dec. 23, 1994), pp. 1961-1966.
Shao, Yong et al., "DNA-templated assembly and electropolymerization of aniline on gold surface", Electrochemistry Communications 4 (2002), pp. 773-779.
Yang, Ning-Sun et al., "In vivo and in vitro Gene Transfer to Mammalian Somatic Cells by Particle Bombardment", Proceedings of the National Academy of Sciences of the United States of America, vol. 87, Issue 24 (Dec. 1990), pp. 9568-9572.
Kovtyukhova, Nina I. et al., "Nanowires as Building Blocks for Self-Assembling Logic and Memory Circuits", Chemistry European Journal, 2002, 8, No. 19, pp. 4355-4363.
Bauer, L.A., et al., "Biological Applications of High Aspect Ratio Nanoparticles", Journal of Materials Chemistry, vol. 14, pp. 517-526 (Jan. 2004).

Tanese, M. et al., "Magnetic Trapping and Self-Assembly of Multicomponent Nanowires", Journal of Applied Physics, vol. 91, No. 10, pp. 8549-8551 (May 2002).
Martin, B.R., et al., "Orthogonal Self-Assembly on Colloidal Gold-Platinum Nanorods", Advanced Materials, vol. 11, No. 12, pp. 1021-1025 (1999).
A. K. Salem, et al., "Receptor-Mediated Self-Assembly of Multi-Component Magnetic Nanowires"; Advanced Materials, vol. 16, No. 3, pp. 268-271 (Feb. 2004).
Tanase, M., et al., "Magnetic Alignment of Fluorescent Nanowires", Nano Letters, vol. 1, No. 3, pp. 155-158 (2001).
Reich, D.H., et al., "Biological Applications of Multifunctional Magnetic Nanowires (Invited)", Journal of Applied Physics, vol. 93, No. 10, pp. 7275-7280 (May 2003).
Mann, S., et al., "Biologically Programmed Nanoparticles Assembly", Advanced Materials, vol. 12, No. 2, pp. 147-150 (2000).
Bauer, L.A., et al., "Selective Funtionalization of Two-Component Magnetic Nanowires", Langmuir, vol. 19, pp. 7043-7048 (May 2003).
Birenbaum, N.S., et al., "Selective Noncovalent Adsorption of Protein to Bifunctional Metallic Nanowire Surfaces", Langmuir, vol. 19, pp. 9580-9582 (Oct. 2003).
Freeman, R.G., et al., "Self-Assembled Metal Colloid Monolayers", An Approach to SERS Substrates, Science, vol. 267, pp. 1629-1632 (Mar. 17, 1995).
Hickman, J.J., et al., "Toward Orthogonal Self-Assembly of Redox Active Molecules on Pt and Au: Selective Reaction of Disulfide with Au and Isocyanide with Pt", Langmuir, vol. 8, pp. 357-359 (1992).
Zhang, Z., et al., "Hydrogen-Bonding Stabilized Self-Assembled Monolayer Film of a Functionalized Diacid, Protoporphyrin IX Zinc(II), onto a Gold Surface", Nano Letters, vol. 1, No. 5, pp. 241-243 (2001).
Karpovich, D.S., et al., "Vapor Adsorption onto Metal and Modified Interfaces: Evidence for Adsorbate Penetration of an Alkanethiol Monolayer on Gold", Langmuir, vol. 13, pp. 4031-4037 (May 1997).
Chen, S.H., et al., "Fluorescence Probe Studies of Self-Assembled Monolayer Films", Langmuir, vol. 7, pp. 1719-1726 (Feb. 1991).
Roy, K., et al., "Oral Gene Delivery With Chitosan-DNA Nanoparticles Generates Immunologic Protection in A Murine Model of Peanut Allergy", Nature Medicine vol. 5, pp. 387-391 (Apr. 1999).
Luo, D., et al., "Synthetic DNA Delivery Systems", Nature Biotechnology, vol. 18, pp. 33-37 (Jan. 2000).

(Continued)

*Primary Examiner*—James Ketter
(74) *Attorney, Agent, or Firm*—Lowenstein Sandler PC

(57) ABSTRACT

This invention is predicated on the present applicants' discovery that nanostructures comprising discrete regions of different composition can be used to deliver to a biological cell a desired combination of molecules in close proximity. Different molecules can be selectively bonded to discrete regions of different composition in sufficiently close physical relationship to enhance delivery or effectiveness within the cell. The preferred nanostructures are multicomponent nanorods. Important applications include delivery of missing DNA sequences for gene therapy and delivery of antigens or DNA encoding antigens for vaccination.

20 Claims, 11 Drawing Sheets
(2 of 11 Drawing Sheet(s) Filed in Color)

OTHER PUBLICATIONS

Pouton, C., et al., "Key Issues In Non-Viral Gene Delivery", Advanced Drug Delivery Reviews vol. 46, pp. 187-203 (2001).

Abdallah, B., et al., "Non-Viral Gene Transfer: Applications In Developmental Biology And Gene Therapy", Biology of the Cell, vol. 85, pp. 1-7 (Nov. 1995).

Prabha, S., et al., "Size Dependency of Nanoparticle-Mediated Gene Transfection: Studies With Fractionated Nanoparticles", International Journal of Pharmaceutics, vol. 244, pp. 105-115 (Jun. 2002).

Whitney, T.M., et al., "Fabrication and Magnetic Properties of Arrays of Metallic Nanowires", Science, vol. 261, pp. 1316-1319 (Sep. 3, 1993).

Wagner, E., et al., "Delivery of Drugs, Proteins and Genes Into Cells Using Transferrin As A Ligand For Receptor-Mediated Endocytosis", Advanced Drug Delivery Reviews, vol. 14, pp. 113-135 (Jul. 1994).

Laibinis, P.E., et al., "Orthogonal Self-Assembled Monolayers: Alkanethiols on Gold and Alkane Caraboxylic Acids on Alumina", Science, vol. 245, pp. 845-847 (Aug. 25, 1989).

Truong-Le, V.L., et al., "Controlled Gene Delivery by DNA-Gelatin Nanospheres", Human Gene Therapy, vol. 9, pp. 1709-1717 (Aug. 10, 1998).

Raychaudhuri, S., et al., "Fully Mobilizing Host Defense: Building Better Vaccines", Nature Biotechnology, vol. 16, pp. 1025-1031 (Nov. 1998).

Hung, CF, et al., "Cancer Immunotherapy Using a DNA Vaccine Encoding The Translocation Domain of a Bacterial Toxin Linked To a Tumor Antigen", Cancer Research, vol. 61, pp. 3698-3703 (May 2001).

Hung, CF, et al., "Improving DNA Vaccine Potency Via Modification of Professional Antigen Presenting Cells", Current Opinion in Molecular Therapeutics, vol. 5, pp. 20-24 (2003).

Salem, A.K., et al., "Mulifunctional Nanorods For Gene Delivery", Nature Materials, vol. 2, pp. 668-671 (Oct. 2003).

Woods, R.K., et al., "Reported Food Intolerance and Respiratory Symptoms in Young Adults", Eruopean Respiratory Journal, vol. 11, pp. 151-155 (1998).

Barnes, R.M.R., "IgG and IgA Antibodies to Dietary Antigens in Food Allergy and Intolerance", Clinical and Experimental Allergy, vol. 25, Suppl. 1, pp. 7-9 (1995).

Macdonald, T.T., "Evidence for Cell-Mediated Hypersensitivity as an Important Pathogenetic Mechanism in Food Intolerance", Clinical and Experimental Allergy, vol. 25, Suppl. 1, pp. 10-13 (1995).

Sun, L., et al., "Magnetic Anisotropy in Prismatic Nickel Nanowires" Applied Physics Letters. vol. 79, No. 26, pp. 4429-4431 (Dec. 2001).

Zelenay, S., et al., "Immunostimulatory effects of plasmid DNA and synthetic Oligodeoxynucleotides", European Journal of Immunology, vol. 33, pp. 1382-1392 (2003).

Krieg, A.M., et al., "Enhancing Vaccines With Immune Stimulatory CpG DNA", Current Opinion in Molecular Therapeutics, vol. 3, pp. 15-24 (2001).

Klimuk, S.K., et al., "Epicutaneous Application of CpG Oligodeozynucleotides With Peptide or Protein Antigen Promotes the Generation of CTL", Journal of Investigative Dermatology, vol. 122, pp. 1042-1049 (2004).

Mutwiri, G.K., et al., "Strategies for Enhancing The Immunostimulatory Effects of CpG Oligodeoxynucleotides", Journal of Controlled Release, vol. 97, pp. 1-17 (Apr. 2004).

Dileo, J., et al., "Gene Transfer To Subdermal Tissues Via a New Gene Gun Design" Human Gene Therapy, vol. 14, pp. 79-87 (Jan. 2003).

Salem, A.K., et al., "Directed Assembly of Multisegment Au/Pt/Au Nanowires" Nano Letters, vol. 4, No. 6, pp. 1163-1165 (2004).

METHODS AND PRODUCTS FOR DELIVERING BIOLOGICAL MOLECULES TO CELLS USING MULTICOMPONENT NANOSTRUCTURES

CROSS REFERENCE TO RELATED APPLICATIONS

This application claims the benefit of U.S. Provisional Patent Application Ser. No. 60/482,141 filed by Dr. Aliasger K. Salem et al on Jun. 24, 2003 and entitled "Multifunctional Nanorods for Gene Delivery", which is incorporated herein by reference.

STATEMENT OF GOVERNMENT INTEREST

This invention was made with government support under DARPA/AFOSR contract number F49620-02-1-0307. The government has certain rights in this invention.

FIELD OF THE INVENTION

This invention relates to methods of delivering biological molecules to cells and, in particular, to methods of delivering to cells a desired combination of biological molecules in close physical proximity. It also includes products for effecting such delivery.

BACKGROUND OF THE INVENTION

The capability of delivering biologically active molecules to plant and animal cells is of great importance to medicine and genetic research and engineering. In medicine, for example, the development of effective vaccines requires systems for providing characteristic portions of infectious biological entities to immune system cells so that the immune system will recognize and fight an infection. When such characteristic portions (antigens) of entities such as viruses, bacteria or even tumors are appropriately provided, the immune systems identifies the antigens as foreign and stimulates development of immunological countermeasures. One way to provide antigens is to deliver them directly into cells. Another way is to deliver to the cells DNA sequences that encode the antigens.

Gene therapy seeks to introduce additional genetic material (typically DNA) into a cell in such a way that the additional genetic material will be functionally incorporated into the existing genetic material of the cell. For example, there are certain diseases that are caused by the absence in cells of normally present DNA sequences (genes) needed to make critical proteins. Gene therapy seeks to alleviate such diseases by providing the cells with the missing DNA sequences so that the cells themselves can provide the critical proteins. To achieve this goal, the missing DNA sequences need to be introduced into cells in such a fashion that they are functionally incorporated into the genetic material and mechanisms of the cells.

The effectiveness of an active biological molecule in a cell often can be enhanced by the presence of one or more additional different molecules. For example, there are molecules, called adjuvants, that will increase the likelihood that an antigen will be recognized as an appropriate target for immunological countermeasures. As another example, there are also molecules that will interact with cell receptors and increase the likelihood of incorporation into the cell. Such enhancing molecules, however, typically must be close to the active molecule in order to enhance its effectiveness.

Conventional approaches to delivering biological molecules to cells leave much to be desired. The common approach to gene therapy is based on the fact that viruses have evolved to inject genetic material into a cell and use the cell's genetic machinery to replicate the viral genetic material. Appropriate modification of the virus might eliminate its harmful features and redirect a viral vector to deliver desirable genetic material into the cell. However virus vectors often generate counterproductive host immune responses and present a risk of killing infected host cells (cytotoxicity).

Other delivery approaches that have been suggested include the use of carriers comprising liposomes, polymers and gold nanoparticles. They have not, however, achieved notable success in efficiently incorporating new genetic material or in making more effective vaccines. Accordingly there Is a need for improved methods and products for delivering biological molecules to cells.

SUMMARY OF THE INVENTION

This invention is predicated on the present applicants' discovery that nanostructures comprising discrete regions of different composition can be used to deliver to a biological cell a desired combination of molecules, including at least one biological molecule, in close proximity. Different molecules can be selectively bonded to discrete regions of different composition in sufficiently close physical relationship to enhance delivery or effectiveness within the cell. The preferred nanostructures are multicomponent nanorods. Important applications include delivery of missing DNA sequences for gene therapy and delivery of antigens or DNA encoding antigens for vaccination, and simultaneous delivery of interacting medicines in specific proportion and close proximity.

BRIEF DESCRIPTION OF THE DRAWINGS

The patent file contains at least one drawing executed in color. Copies of this patent with color drawing(s) will be provided by the Office upon request and payment of the necessary fee.

The advantages, nature and various additional features of the invention will appear more fully upon consideration of the illustrative embodiments now to be described in detail in connection with the accompanying drawings. In the drawings:

In FIG. 2a nanorods are incubated with the 3-[(2-aminoethyl)dithio]propionic acid (AEDP) linker. The carboxylate end group binds to the nickel segment. The disulfide linkage at the center acts as a cleavable point within the spacer promoting DNA release within the reducing environment of the cell. In FIG. 2b plasmids are bound by electrostatic interactions to the protonated amines presented on the surface of the nickel segment. In FIG. 2c calcium chloride compacts the plasmids encoding the luciferase or GFP reporter genes; and in FIG. 2d rhodamine-conjugated transferrin presenting sulfhydryl groups is selectively bound to the gold portion of the nanorods.

FIG. 3a is a visible light image of dual functionalized 200 nm long Au/Ni nanorod. FIG. 3b fluorescence image of the rhodamine-tagged (543/570 nm) transferrin on the Au segment. FIG. 3c is a fluorescence image of the Hoechst stained (350/450 nm) plasmids on the Ni segment; and FIG. 3d is a fluorescent overlay image combining FIGS. 3b and 3c.

FIG. 4a presents stacked laser scanning confocal microscope images of a live HEK293 cell (red/633 nm, green/543 nm). Rhodamine (633 nm) identifies the sub-cellular location of the nanorods whilst GFP expression (543 nm) provides confirmation of transfection throughout the cell. FIGS. 4b and 4c are, orthogonal sections that confirm the nanorods are within the cell. FIG. 4d shows confocal microscope stacked images, of a live HEK 293 cell stained with Lysotracker Green identifying the location of the nanorods (Rhodamine) in relation to acidic organelles in both orthogonal sections (FIGS. 4e and 4f).

FIG. 5a is a SEM image of HEK293 cells after Ih incubation with 200 nm Au/Ni nanorods. FIG. 5b is a back-scattering SEM image of 200 nm Au/Ni nanorods after 4 h incubation showing the nanorods beneath the surface of the cell. FIG. 5c is a TEM cross-sectional image showing the intra-cellular location of the nanorods after 4 h incubation, and FIG. 5d is a, SEM image of 200 nm long nanorods after 4 h incubation.

FIG. 6a shows percentage of GFP expression (area of cells fluorescing/total cell area) and FIG. 6b shows luciferase expression of: 1. nanorod-plasmid complex, 2. nanorod-plasmid/transferrin complex, 3. nanorod-plasmid/transferrin complex incubated with 100 micromoles chloroquine, 4. Lipofectamine (positive control) and 5. naked DNA (negative control).

FIG. 11a is a back-scattering SEM image of nanowires showing integrity of Au, Ni and Pt segments. The image confirms platinum segments are longer than Ni and Au segments. FIGS. 11b and 11c light and fluorescence microscope images of Au/Ni/Pt nanowires functionalized with BIC and Rhodamine Red-12-dodecanoic acid (Ex 570, Em 590). Confirmation of selective derivatisation of Au/Ni/Pt nanowires with BIC, Rhodamine Red-12-dodecanoic acid and Marina Blue-1-undecane-thiol is observed by light microscope images (FIG. 11d) and fluorescence microscope images FIGS. 11e-11g. FIG. 11d is a light microscope image of a functionalized Au/Ni/Pt nanowire. FIG. 11e shows the fluorescence from the Marina Blue-1-undecane-thiol (Ex 365, Em 460) bound to the gold segment. FIG. 10e shows the fluorescence from the Rhodamine Red-12-dodecanoic acid (Ex 570, Em 590) from the nickel segment, and FIG. 11g is a fluorescent overlay image combining 10e and 10f.

It is to be understood that these drawings are for illustrating the concepts of the invention and, except for the graphs, are not to scale.

DETAILED DESCRIPTION

Figure 1:
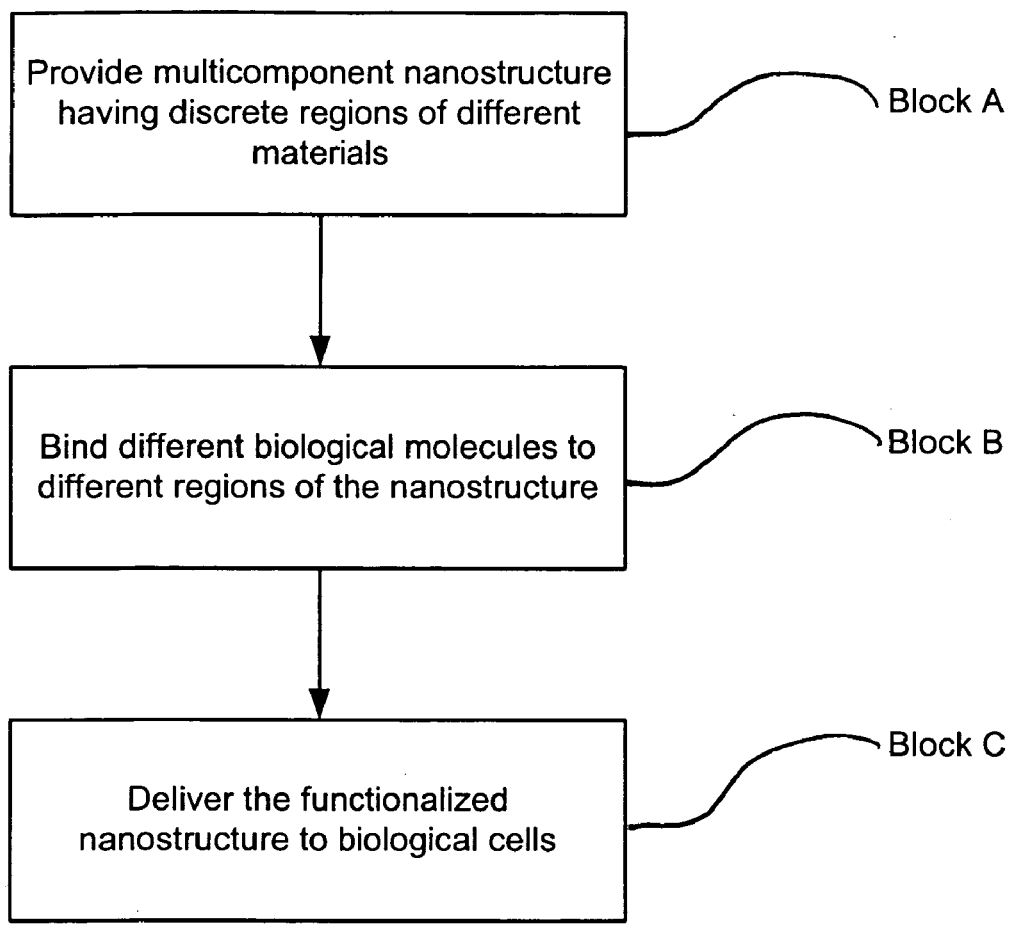
FIG. 1 is a schematic block diagram of a method of delivering biological molecules to cells in accordance with the invention.

Referring to the drawings, FIG. 1 is a schematic block diagram of a method for delivering biological molecules to cells in accordance with the invention. As shown in Block A, an initial step is to provide a multicomponent nanostructure comprising at least two discrete regions of respectively different materials. The term "nanostructure" as used herein refers to structures having maximum dimensions in at least two dimensions that are substantially smaller than the diameter of a cell so that the structures may enter a cell without destroying its functionality. Typically the nanostructure has two maximum dimensions of less than about 500 nanometers and preferably less than about 200 nanometers. The maximum third dimension is also preferably less than the diameter of a cell so that the nanostructure can be incorporated in the cell, but it can be greater (into the micrometer range) and still transfect a cell. Useful multicomponent nanostructures have at least two discrete regions large enough to bind respective biological molecules but positioned sufficiently close together that both molecules can be delivered into the same cell at the same time.

The inventive method can use multicomponent nanostructures in a wide variety of sizes and shapes including multicomponent nanorods, nanowires, nanotubes, nanoscale bars, nanodisks, nanoscale ovals, nanoscale parallelpipeds and multicomponent nanoparticles of regular or irregular shape. Multicomponent nanostructures with any one of a wide variety of shapes, sizes and material combinations can be fabricated by techniques well known in the art, as by depositing successive nanolayers on a removable substrate, patterning the layers by nanoimprint lithography, and removing the substrate. Further details concerning nanoimprint lithography can be found, for example, in U.S. Pat. No. 6,309,580 issued to Stephen Chou on Oct. 30, 2001, which is incorporated herein by reference.

Figure 2:
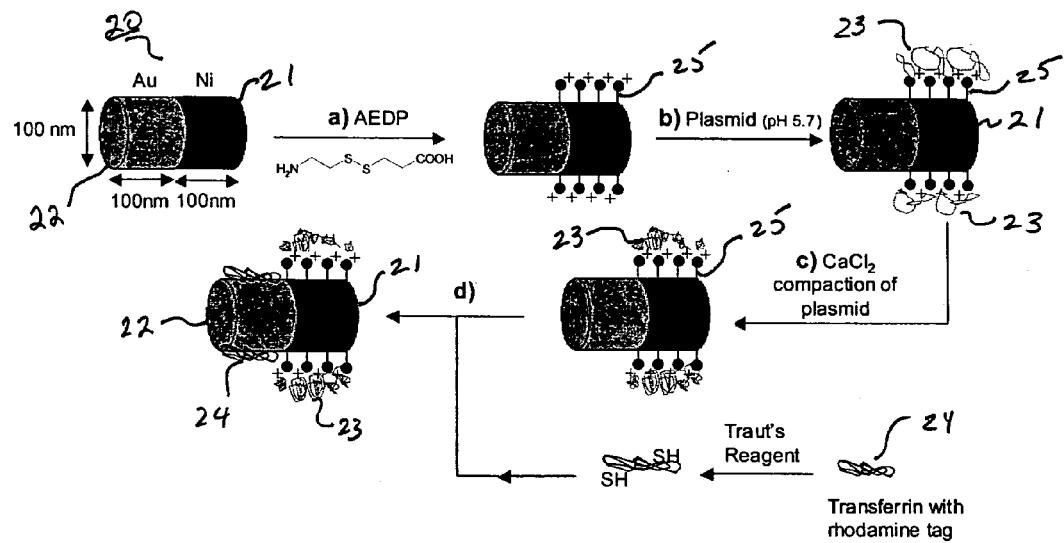
FIG. 2 is a schematic diagram illustrating functionalization of multicomponent nanostructures.

The preferred multicomponent nanostructures are nanorods or nanowires comprised of discrete segments of respectively different materials (See FIG. 2). Such segmented rods or tubes can be fabricated, for example, by electro-depositing successive layers of different metals in a nanoporous matrix material and removing the matrix material, as by selectively dissolving in acid or base.

The next step shown in Block B is to attach one or more molecules of different materials to the respectively different discrete regions of the nanostructure. In essence, each different molecule is provided with a chemical group that selectively bonds to a respetively different material of the multicomponent nanostructure. The preferred molecules for attachment are biological molecules. The term "biological molecules" as used herein includes, without limitation, molecules of genetic material (DNA and RNA), molecules of materials that activate cell receptors (external or internal), antigens or their genetic material, and materials that enhance the incorporation of genetic material or stimulate the immune response. The term also includes molecules of medications that are active at the cellular level, and especially different medications that have a synergistic effect when delivered together. Thus, for example, molecules to stimulate cell receptors can be selectively bonded to a first material segment of a nanorod and a DNA sequence can be selectively bonded to a second material segment. As another example, DNA encoding an antigen can be selectively bonded to a first segment and an immune system stimulating adjuvant molecule can be bonded to a second segment, and an antigen can be bonded to a yet third segment. Exemplary of useful RNA biological molecules is siRNA that can be used to silence undesirable genes. Thus a multicomponent nanostructure could contain RNA to silence a defective gene and DNA to provide the correct gene. An example of synergistic medications that could be simultaneously delivered by multicomponent nanostructures include Taxol and Discodermolide.

The third step, Block C, is to deliver the nanostructure and its bonded molecules to biological cells. The method of delivery may depend on the location and type of cells. For delivery to somatic cells, the preferred approach is to use a nanostructure including a bonded biological molecule to stimulate cell receptors that will take the structure into the cell. The nanostructures can be introduced, as by pneumatic injection, into desired tissues and stimulated cell receptors will facilitate their intake into cells. For dendritic cells located near the surface of the body, the nanostructures may be injected directly into the cells as by pneumatic pressure. Deeper penetration into somatic cells may be achieved by orienting nanotubes so that their cylindrical axes are aligned approximately perpendicular to the target tissue at the point of injection.

As will be illustrated in the exemplary embodiments described herein below, a major advantage of this method is the ability to simultaneously provide specific combinations of biological molecules in close adjacency where they can interact to produce more effective biological results, e.g. more effective incorporation in the cell, an enhanced immune response, or a more effective combination of medicines.

The invention can now be more clearly understood by consideration of the following examples.

EXAMPLE 1

Delivery of Genetic Material for Gene Therapy

The goal of gene therapy is to introduce foreign genes into somatic cells to supplement the defective genes or to provide additional biological functions. Gene transfer ("transfection") can be achieved using either viral or synthetic non-viral delivery systems ("vectors"). While viral vectors exhibit high efficiency, synthetic transfection systems provide several advantages including ease of production and reduced risk of cytotoxicity and immune response. Much of the poor transfection efficiency of non-viral vector stems from the difficulty of controlling their properties at the nanoscale. One aspect of the present invention is a novel non-viral delivery system based on nanostructures that can simultaneously bind compacted DNA plasmids and target cell receptors for enhanced internalization. The present example demonstrates the potential of this system to deliver genetic material with precise composition and size control.

Achieving efficient gene delivery into a target cell population or tissue without causing associated toxicity is critical to the success of gene therapy. To this end, both viral and non-viral vectors have been extensively investigate. Although viral vectors such as adenovirus, lentil virus, influenza virus, and adeno-associated virus are efficient in transfecting cells, their toxicity and immunogenicity remain severe limitations.

As alternatives to viruses, non-viral vectors such as liposomes and polymers have been increasingly studied to overcome this long-term safety issue. In contrast, inorganic gene carriers have received limited attention in the gene therapy community. Gold nanoparticles with bound DNA are used in particle bombardment-mediated gene transfer ("gene gun technology"). While this gene gun technology may be effective in transfecting cells in the skin for genetic immunization, it has limited utility in general gene transfer applications involving internal organ transfection.

To be effective, non-viral vectors must gain entry into the target cells and then release the condensed plasmid into the cytoplasm for translocation into the nucleus. To date, particle-based vectors have been formulated by using polycationic polymers or lipids to condense DNA into nano-complexes that can be internalized by cells. The size of these nano-complexes is typically difficult to control and widely dispersed. Targeting ligands can be conjugated to the carrier or complexes either pre- or post-complexation with the DNA from the complexes may also become a rate-limiting step. To optimize these different aspects in designing an effective non-viral gene delivery system has been a major challenge in the field.

The possibility of achieving control of size and composition by inorganic synthesis has prompted us to evaluate the potential of multi-segment metallic carriers in gene delivery. In this example, we demonstrate the novel properties of bi-functional Au/Ni nanorods in gene transfer. Deposition of the Au/Ni nanorods was achieved by template synthesis. This technique involves electrochemical deposition into a non-conducting membrane having an array of cylindrical pores and has been used for the synthesis of a wide range of materials and structures. Template synthesis is preferred over other techniques because it is easily adapted for the deposition of multiple sub-micron segments. Furthermore, template synthesis can produce large quantities of monodisperse nanorods, and properties such as aspect ratio can be controlled in a systematic way.

Referring to FIG. 2, the nanorods 20 were fabricated by electrodeposition into an $Al_2O_3$ template (Anodisc, Whatman) with a pore diameter of 100 nm. An evaporated silver film on one side of the template served as the working electrode in a three-electrode configuration. A thin layer of silver was electrodeposited into the template from 50 mM $KAg(CN)_2$, 0.25 M $Na_2CO_3$ buffered to pH 13 at a potential of −1.0V (Ag/AgCl) and Ni segments 21 were deposited from a solution of 20 g $L^{-1}$ $NiCl_2.6H_2O$, 515 g $L^{-1}$ $Ni(H_2NSO_3)_2.4H_2O)$, 20 $gL^{-1}H_3BO_3$ buffered to pH 3.4 at a potential of −1.0 V (Ag/AgCl) to ensure easy release of the nanorods from the template. The Au segments 22 were deposited from a commercial gold plating solution (Technic Inc.) at a potential of −1.0V (Ag/AgCl) and the Ni segments 21 were deposited from a solution of 20 $gL^{-1}$ $NiCl_2.6H_2O$, 515 $gL^{-1}$ $Ni(H_2NSO_3)_2.4H_2O)$, 20 $gL^{-1}H_3BO_3$ buffered to pH 3.4 at a potential of −1.0 V (Ag/AgCl). The silver layers were dissolved in 70 vol % nitric acid and the alumina template was then dissolved in 2 M potassium hydroxide. The nanorods 20 were washed repeatedly using 2 M potassium hydroxide, de-ionized water and ethanol. The nanorods were 100 nm in diameter and 200 nm in length with 100 nm gold segments and 100 nm nickel segments.

Using molecular linkages that bind selectively to either gold or nickel, we have attached DNA 23 and a cell-targeting protein 24, transferrin, to the different segments, as shown schematically in FIG. 2. Transferrin was one of the first proteins to be exploited for receptor-mediated endocytosis of the transferrin-iron complex. The transferrin 24 was bound to the gold segments 22 of the nanorods 20 through a thiolate linkage (not shown), by converting a small proportion of the primary amine groups of transferrin to sulfhydryl groups. A rhodamine tag (not shown) on the transferrin provided a mechanism for confirmation of internalization and intracellular tracking of the nanorods.

DNA 23 was bound to the nickel segments 21 by suspending the dual component nanorods in a 0.1 M solution of 3-[2-aminoethyl)dithio]propionic acid (AEDP). The carboxylic acid terminus of AEDP binds to the native oxide on the nickel segments. This resulted in the surface presentation of primary amine groups spaced by a reducible disulfide linkage 25. Plasmids encoding the firefly luciferase (pCMV-luciferase VR1255_C) with 6.413 kb driven by the cytomegalovirus (CMV) promoter/enhancer (luciferase-plasmid) or plasmids encoding the GFPmut1 variant (PEGFP-C1) with 4.7 kb driven by the SV40 early promoter (GFP-plasmid) were conjugated to the AEDP bound to the nickel segments 21 of the nanorods 20 at pH 5.7. The plasmid concentration, determined from absorbance spectroscopy, was about $4 \times 10^{12}$ molecules $cm^{-2}$.

To further compact the DNA bound to the nanorods for more efficient cell entry and protection of the DNA from enzymatic degradation, the nanorods were incubated in 2M $CaCl_2$ after excess non-bound plasmids had been removed. $Ca^{2+}$ has a high affinity to DNA ($K_d$ of $1.1 \times 10^{-3} M^{-1}$), forming $CaPO_4$ complexes with the nucleic backbone to provide stabilization and compaction to the DNA structure.

Confirmation of the selective binding of transferrin and plasmid was obtained by fluorescence microscopy. Since the 200 nm long nanorods cannot be seen by optical microscopy, these experiments were performed on 20 micron long and 100 nm diameter nanorods with Ni and Au segments of equal length.

Figure 3:
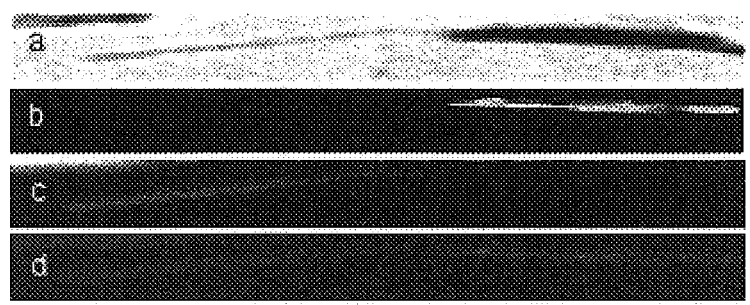
FIG. 3 shows microphoto images pertaining to functionalized multicomponent nanostructures.

FIG. 3 shows uniform red fluorescence from the rhodamine-tagged transferrin on the gold segments and uniform blue fluorescence from the Hoechst, which selectively binds to the DNA conjugated to the nickel segments.

To evaluate the gene delivery potential of these dual functionalized Au/Ni nanorods, in vitro transfection experiments were performed on the Human Embryonic Kidney (HEK293) mammalian cell line with the GFP and luciferase reporter genes, respectively. For transfection, the nanorods were incubated with HEK293 cells at a dosing level ($4.4 \times 10^{-5}$ mg $mL^{-1}$) significantly below the cytotoxicity (LD50) value for 4 hours in Opti-MEM cell culture medium (Gibco BRL, Rockville, Md.). Following washing, cells were further incubated in serum-containing media for two days.

Figure 4:
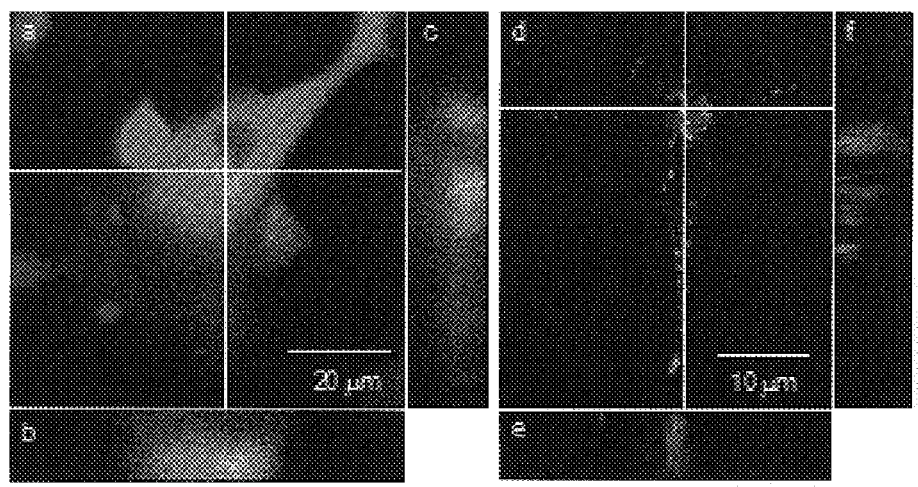
FIG. 4 shows microphoto images of cells transfected in accordance with the method of FIG. 1.

FIG. 4 shows confocal microscopy sections of cells following transfection. FIG. 4a shows the characteristic green fluorescence from the GFP expressed by the cells as a result of tranfection. Superimposed on the GFP emission is the red emission from the rhodamine conjugated to the Au segments of the nanorods. The orthogonal sections show clearly that the nanorods are located in the cell. FIG. 4d shows fluorescence images from cells after 4 h incubation that have been stained with Lysotracker green revealing that the nanorods are located in or around acidic organelles.

Figure 5:
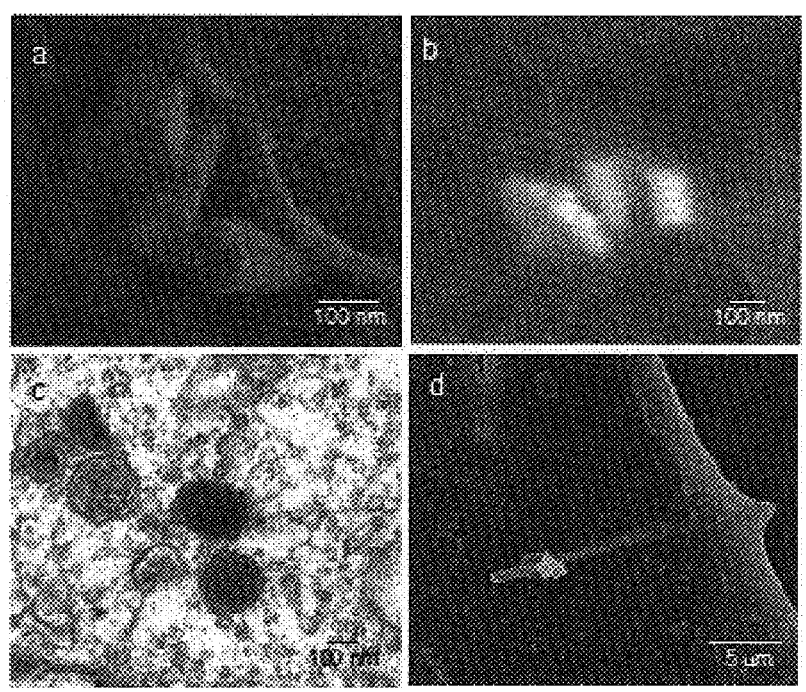
FIG. 5 presents scanning electron microscope images of cells transfected in accordance with the method of FIG. 1.

The uptake of the nanorods by HEK293 cells is shown in the scanning electron microscope images in FIGS. 5a and 5b, after 1 and 4 hours incubation, respectively. Transmission electron microscope images (FIG. 5c) showed that nanorods were located in vesicles or the cytoplasm but not the nucleus. This suggests that transfection is due to plasmids released or cleaved from the nanorods prior to nuclear entry. In contrast, 20 µm long nanorods were found only partially internalized after 4 hours (FIG. 5d) presumably because of size constraints.

To further understand the transfection mechanism, a series of experiments were undertaken to compare the two-component nanorods with and without transferrin and chloroquine. Chloroquine is an endosomolytic agent widely used to promote escape of the sequestered complexes from endosomal into cytoplasmic compartments.

Figure 6:
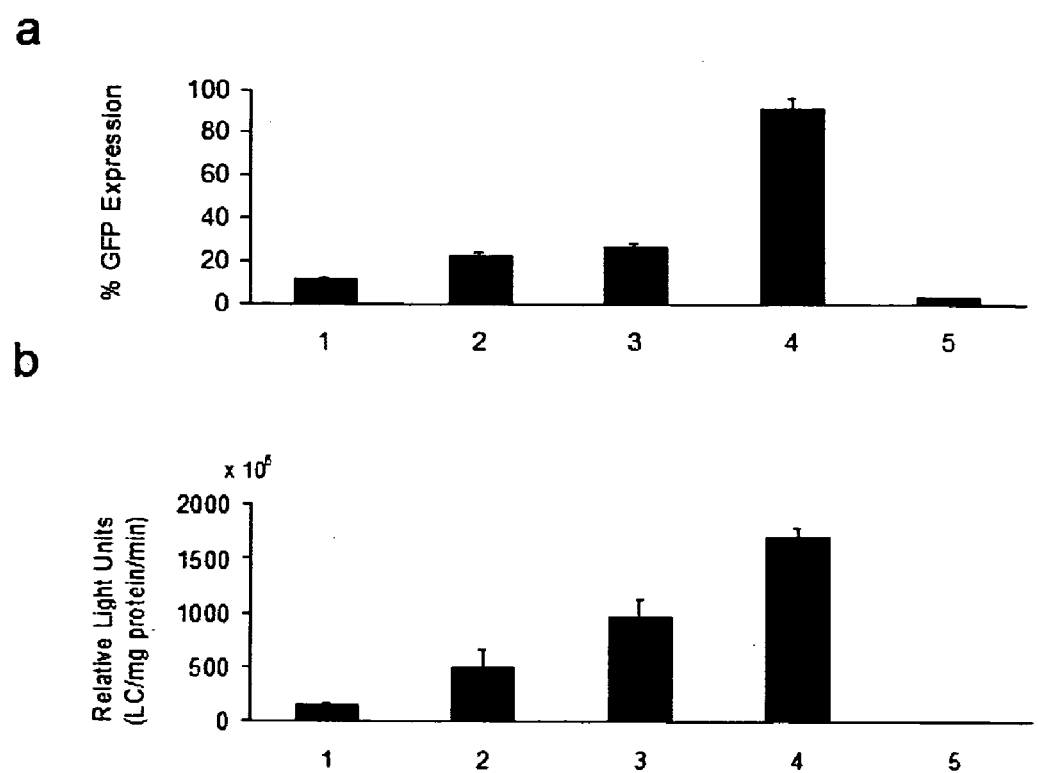
FIG. 6 is a set of histograms summarizing results of transfection experiments.

FIG. 6 summarizes the transfection experiments. A significantly higher fraction of cells expressed GFP when transfected with plasmid-nanorods than with naked DNA, which was <3%. Comparing with the luciferase plasmid, transfection by nanorods shows a 255-fold higher expression than naked DNA. Nanorods with transferrin produced 22% of GFP-positive cells, 2 times higher than those with transferring; the enhancement is 3.4 times for luciferase expression level. Addition of chloroquine to nanorods with transferrin further improved GFP expression to 27% of positive cells, and increased the luciferease expression level by a factor of 1.9. The fact that chloroquine enhances transferrin-mediated transfection suggests that receptor-mediated endocytosis is involved. Chloroquine may also enhance transfection by protecting against DNA degradation.

To confirm that transfection was due to intracellular rather than extracellular release of plasmids, nanorods complexed with the luciferase-plasmid were incubated in serum-containing media. The supernatant was removed at various time points from 15 minutes to 4 hours and used to transfect the HEK293 cells. In all cases no significant transfection above background could be detected in these samples. These data confirm that the transfection detected is a result of the intracellular released plasmids from the 200 nm nanoraods. Further details concerning the methods and materials of Example 1 are set forth in Appendix A attached hereto.

In summary, this example demonstrates a new approach for gene delivery using multi-segment nanorods. Using molecules with end-groups that selectively bind to different metals, specific functionalities can be introduced to individual segments in the nanorod. Here we have used differential binding to attach plasmids and a cell-targeting protein to spatially separated regions of the delivery system. This approach can be extended to include other components that allow additional functionalities to be introduced. For example, an additional segment could be used to bind an endosomolytic agent. In addition to components that allow selective binding, other functions can also be exploited. For example, an external magnetic field can be used to manipulate nanorods with magnetic segments. In addition, the introduction of segments of semiconductor materials can be used to track individual nanorods through their characteristic absorbance or photoluminescence. The ability to configure different segments in varying combinations and with different segment lengths can also be used to barcode individual nanorods. These properties can be exploited to externally control gene delivery in vivo. Thus, this versatile synthetic gene delivery system may help realize the potential of non-viral gene therapy.

EXAMPLE 2

Vaccinations

The goal in genetic vaccinations is to encode cells to transiently manufacture antigens that are subsequently taken up by macrophages or dendritic cells (key antigen presenting cells or APCs). APCs process these antigens via class I or class II pathways where they bind to major histocompatibility complexes that present the antigen on the surface of the APCs. These APCs then move to the lymphoid organs where T lymphocytes that scavenge the surfaces of the APCs become stimulated to respond against the antigen presented. When, for example, the encoded antigen is tumor specific a strong CD8+ and CD4+ T-cell and antibody response can be generated for protection and prevention against that tumor. The inorganic nanorod vectors described herein can generate strong but transient transgene expression when bombarded into skin, which has natural abundance of antigen presenting cells. These nanorods therefore have potential for vaccination applications. In contrast to other inorganic non-viral vectors, these nanorods can be engineered with different functionalities in spatially defined regions, which lead to the potential for precise control of antigen: adjuvant ratios and the possibility of stimulating multiple immune responses. However, before these unique nanorod properties can be exploited for further development, it is essential to ensure that the nanorods can generate a strong versatile immune response in vivo.

In this example, we evaluate the CD4+ antibody and CD8+ T-Cell responses from particle bombardment of nanorods delivering the model antigen ovalbumin or plasmids encoding ovalbumin. Ovalbumin is involved in a number of conditions related to children. For example, children with cystic fibrosis display higher anti-ovalbumin antibodies. Ovalbumin antibodies are also observed in kidney diseases such as nephropathy. Children with insulin dependent diabetes mellitus show elevated immune responses to both β-lactoglobulin and ovalbumin, which may be associated with the progression of the disease.

The nanorods were fabricated by electrodeposition into an $Al_2O_3$ template (Anodisc, Whatman) with a nominal pore diameter of 100 nm. An evaporated silver film on one side of the template served as the working electrode in a three-electrode configuration. A thin layer of silver was electrodeposited into the template to ensure easy release of the nanorods from the template. Au segments were deposited prior to nickel segments to prevent erosion of the nickel layers during silver removal. The silver layers were dissolved in 70 vol % nitric acid and the alumina template was then dissolved in 2 M potassium hydroxide. The nanorods were 1.6 µm in length by 170 nm in diameter with 800 nm length gold segments and 800 nm length nickel segments.

Confirmation of deposition of the nickel and gold segments was seen by back-scattering SEM. Using chemical moieties that bind selectively to either gold or nickel, we attached plasmids of the antigen ovalbumin, to the different segments as described previously. A small proportion of the primary amine groups of ovalbumin were converted to sulfhydryl groups. The ovalbumin was then bound to the gold segments of the nanorods through a thiolate linkage. Electrostatic interactions were used to bind DNA to the nickel segments by suspending the dual component nanorods in a 0.1 M solution 3-[(2-aminoethyl)dithio]propionic acid (AEDP). The carboxylic acid terminum of AEDP binds to the native oxide on the nickel segments. This results in the surface presentation of primary amine groups spaced by a reducible disulfide linkage. In the reducing environment of the cell, the disulfide linkage between the plasmid and the nanowire is cleavable, enhancing release of the plasmid. In this example, plasmids encoding ovalbumin (pcDNA3-OVA7) or control plasmids with blank inserts (pcDNA3) were utilized. Previous UV-visible spectroscopy calibration measurements (260 nm) of DNA binding to the nanowires provided an average surface coverage of $4 \times 10^{12}$ molecules/$cm^2$. For condensation of the plasmids bound to the nanowires, a $CaCl_2$ solution was added to the nanowire-plasmid formulations. $Ca^{2+}$ has a high affinity to DNA ($K_d$ of $1.1 \times 10^{-3} M^{-1}$), forming $CaPO_4$ complexes with the nucleic backbone to provide stabilization and compaction to the DNA structure.

Figure 7:
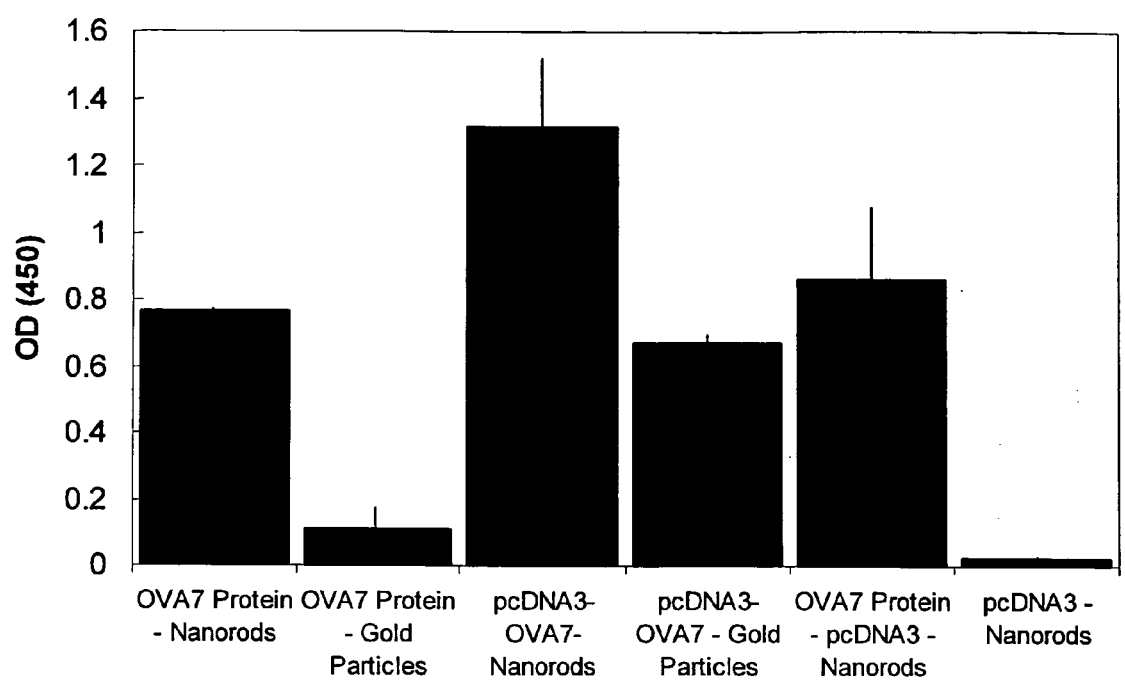
FIG. 7 is a graphical illustration of ovalbumin-specific antibody responses in C57BL/6 mice immunized with various antigen or plasmid nanorod and gold particle formulations. C57BL/6 mice were immunized with control plasmid (no insert) bound to nanorods, ovalbumin antigen-nanorod formulation, ovalbumin antigen-gold particle formulation, pcDNA3-OVA7-nanorod formulation, pcDNA3-OVA7-gold particle formulation and ovalbumin antigen/control pcDNA3 (no insert)-nanorod formulation via a gene gun. Serum samples were obtained from immunized mice 21 days after the initial vaccination. The presence of the ovalbumin-specific antibody was detected by ELISA using serial dilution of sera. The results from the 1:1000 dilutions are presented showing the mean absorbance (A450 nm) ±SE.
Figure 8:
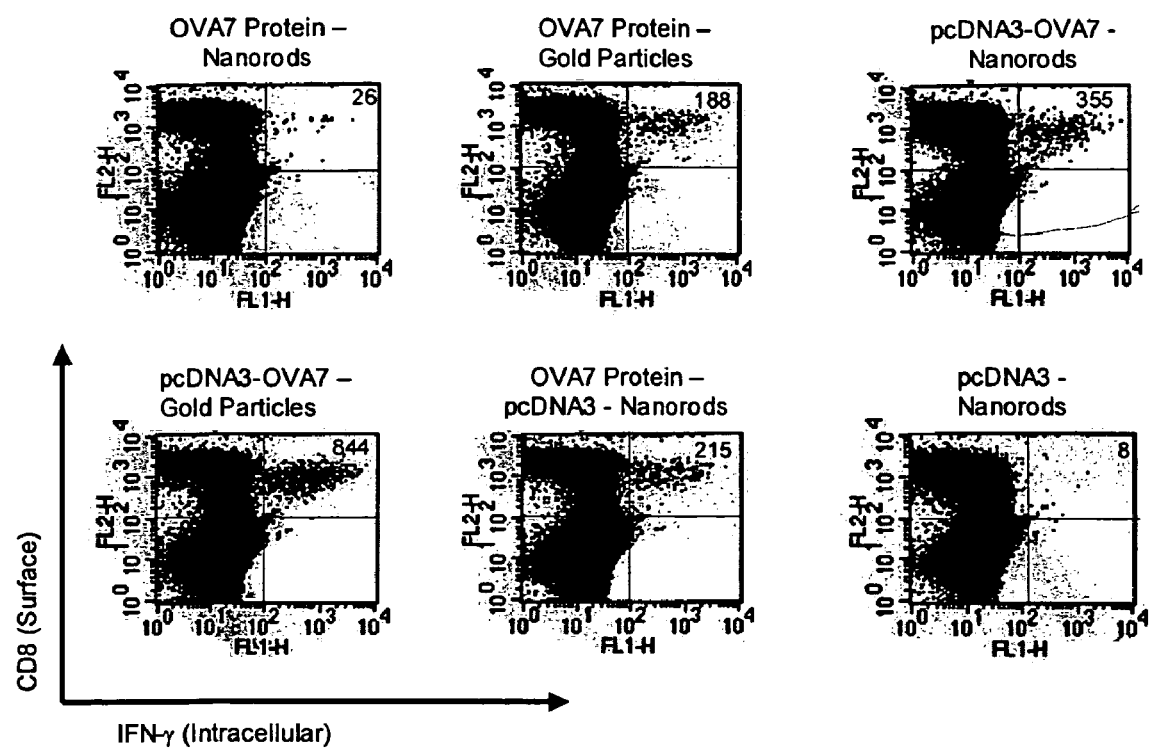
FIG. 8 graphicallly illustrates ovalbumin-specific CD8+ T-cell precursors in C57BL/6 mice immunized with various antigen or plasmid-nanorod and gold particle formulations. C57BL/6 mice were immunized with control plasmid (no insert) bound to nanorods, ovalbumin antigen-nanorod formulation, ovalbumin antigen-gold particle formulation, pcDNA3-OVA7-nanorod formulation, pcDNA3-OVA7-gold particle formulation and ovalbumin antigen/control pcDNA3 (no insert) nanorod formulation via a gene gun. For vaccinated mice, 2 μg of DNA or antigen/mouse were given twice. Splenocytes were harvested 7 days after the last DNA/antigen vaccination. Flow cytometry analysis: Splenocytes from vaccinated mice were cultured in vitro with the ovalbumin antigen overnight and were stained for both CD8 and intracellular IFN–. The number of IFN– secreting CD8+ T-cell precursors in mice immunized with antigen or plasmid-nanorod and gold particle formulations were analyzed by flow cytometry. The number of CD8+ IFN–+ double-positive T cells in $3\times10^5$ splenocytes are represented by the quadrant in the upper right corner.

To evaluate the genetic vaccination potential of these nanorods, CD4+ antibody responses from the bloodstream and CD8+ T-cell responses from the spleen were measured from C57BL/6 mice vaccinated with the nanorod/plasmid or nanorod/antigen formulations. In addition, we compared these responses to the industrially optimized gold particle formulations as analogous responses are essential for the future development of these nanorods in clinical applications. For antigen/microcarrier formulations, the gold particles generated a 7-fold higher CD8+ T-cell response that the nanorods. In contrast, for the CD4+ antibody response, the nanorods produced a 7-fold higher response in comparison with the 1.6 µm gold particles (FIGS. 7 and 8). To evaluate the benefit of the nanorods multifunctionality, pcDNA3 was bound to the nickel segments of the nanorods in conjunction with the ovalbumin-SH antigen on the gold segments. In control experiments, pcDNA3 bound to the nanorods alone generated very low or no CD4+ antibody and CD8+ T-cell responses. However, co-addition of pcDNA3 and the ovalbumin antigen on the nanorods generated a significant 8-fold increase in the CD8 response in comparison to the nanorods bound to the ovalbumin alone. This increase is likely to be due to a role of the CpG motif in the pcDNA3 acting as a strong immunostimulatory adjuvant to the ovalbumin antigen thus enhancing the overall CTL immune response. The nanorods ability to deliver the CpG motif and the antigen to the same cell is essential for generating a stronger immune response. For example, Babuik and colleagues have shown that in pigs, administration of CpG ODN and HBsAg vaccine in separate sites of the same muscle did not show an enhanced antibody response compared to administration of the HBsAg vaccine alone, whereas administration of CpG ODN with the HBsAg vaccine significantly enhanced the antibody responses.

Delivering plasmids encoding ovalbumin by both nanorods and gold particles generated stronger CD4 and CD8 responses than the ovalbumin antigen alone Gene gun delivery of antigens can directly enter and prime dendritic cells, but the delivery of plasmids encoding the antigen probably enhances the overall response because in addition to direct priming of dendritic cells, keratinocytes also become transfected. The keratinocytes then produce antigens that, once released, cross-prime more dendritic cells thereby enhancing overall immune response. Further details concerning the methods and materials of Example 2 are set forth in Appendix B hereto.

In summary, this example that nanorod based vaccines generate strong CD4+ antibody and CD8+ T-cell responses and therefore have significant potential for further development in vaccination applications. We contemplate that aligning the nanorods within the cartridges to produce "arrow" like delivery will allow us to achieve greater depths of penetration in particle bombardment than the gold particles. Advantages to this would include transfecting both skin and the subcutaneous tissues for pressure modulated control over sustained or transient expression of genes and greater depths of penetration at lower pressures. The ability to add new components to the nanorods such as adjuvants and/or cytokines in controlled ratios will allow us to generate stronger immune responses than single component particles as demonstrated in this example using the CpG motif from the pcDNA3 as an immunostimulatory adjuvant to the antigen. In addition, the ability to engineer and add extra segments to the nanorods will allow for the possibility of delivering multiple agents such as RNA, antigens and DNA to the same cell for the stimulation of multiple immune responses.

EXAMPLE 3

Delivery of Multiple Active Molecules

This example demonstrates the selective derivatization of three segment Au/Ni/Pt nanowires using metal specific ligands. By taking advantage of the individual metal segments' affinity to unique functional groups, we show that Au/Ni/Pt nanowires can be functionalised with a thiol linkage on the gold segments, an isonitrile linkage on the platinum segment and a carboxylate linkage on the nickel segment. Selective functionalisation of the Au, Ni and Pt segments is achieved by first functionalizing the Ni segment with carboxylic acid terminated ligands and the Au and Pt segments with an isonitrile terminated ligand. Carboxylic acids have been found to bind to nickel surfaces at an adduct formation constant of $6\pm5\times10^6$ M$^{-1}$. Isonitrile groups are reported to form monolayers on both Au and Pt surfaces. The isonitrile groups on the Au surface can then be selectively substituted with thiol terminated ligands.

Figure 9:
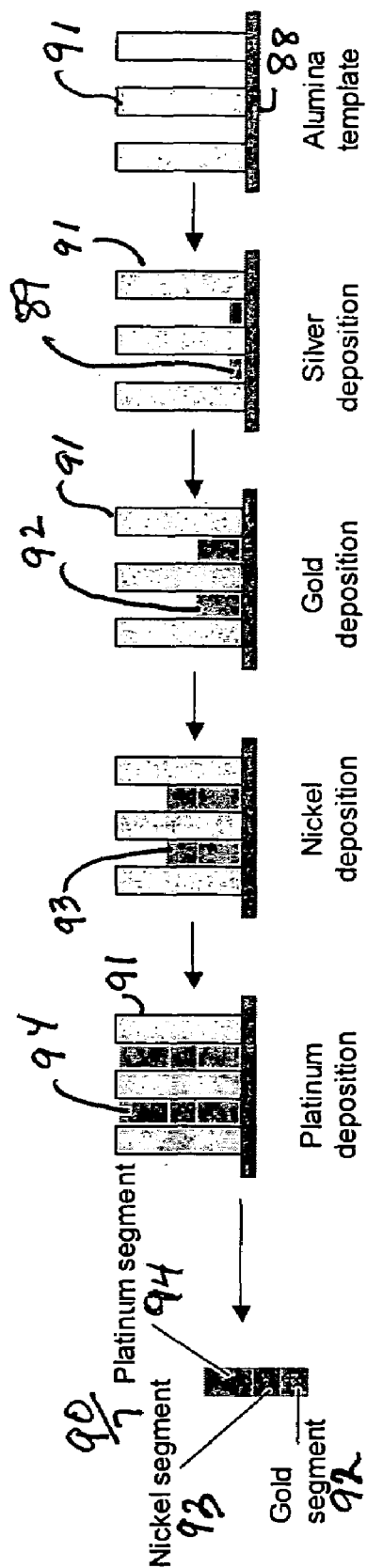
FIG. 9 schematically illustrates formation of three component nanowires.

The formation of three component nanowires is shown in FIG. 9. Au/Ni/Pt nanowires 90 are fabricated by electrodeposition into an $Al_2O_3$ template 91 (Anodisc, Whatman) with a nominal pore diameter of 100 nm. An evaporated silver film 88 on one side of the template serves as the working electrode in a three-electrode configuration. A thin layer of silver 89 is first electrodeposited from 50 mm KAg(CN)2 and 0.25 M $Na_2CO_3$ buffered to pH 13 at –1.0 V (Ag/AgCl) in order to ensure easy release of the nanorods from the template. The Au segments 92 of the nanowires are deposited from a commercial gold plating solution (Technic) at –1.0 V (Ag/AgCl), and the Ni segments 92 are deposited from a solution of 20 g L$^{-1}$NiCl$_2$.6H$_2$O, 515 g L$^{-1}$Ni (H$_2$NSO$_3$)$_2$ .4 H$_2$O, 20 gL$^{-1}$H$_3$BO$_3$ buffered to pH 3.4 at a potential of –1.0 V (Ag/AgCl). The Pt segments 94 are deposited from a solution of 0.015M of (NH$_4$)$_2$.PtCl$_6$ and 0.2M Na$_2$HPO$_4$.7H$_2$O at –0.4 V (Ag/AgCl). The gold segments 92 are deposited before the nickel segments 93 in order to ensure that the nickel segments 93 are not etched by the nitric acid during removal of the silver, and the platinum segments 94 are deposited after the nickel and with longer length segments to clearly differentiate the segment from the gold. The silver layers (88, 89) are dissolved in 70 vol. % nitric acid and the alumina template 91 is then dissolved in 2 M KOH. The nanowires 90 are washed repeatedly using 2 M KOH, de-ionized water, and ethanol. The nanowires 90 are on average 170 nm+/–23 nm in diameter and 8-10 µm in length.

Figure 11:
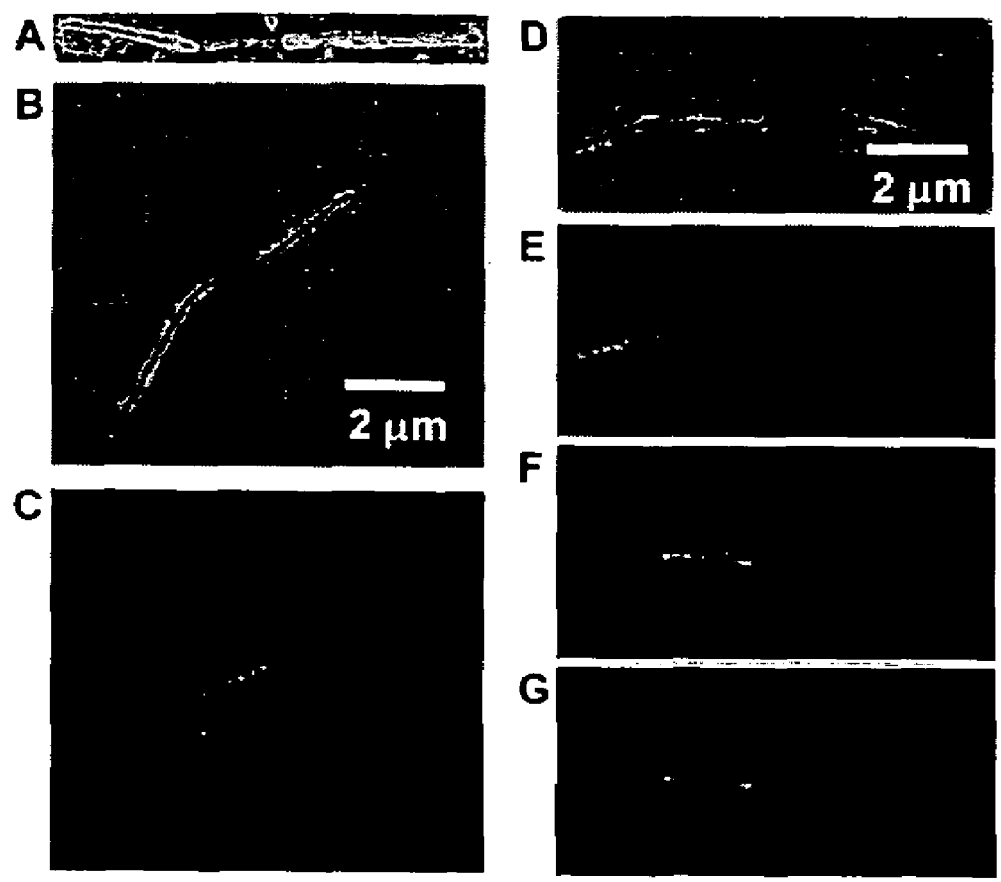
FIG. 11 is a set of micrographs illustrating 3 component nanostructures.

Confirmation of the integrity of the three segments is observed by back-scattering SEM (FIG. 11a). Collection of the nanowires by centrifugation at 8000 rpm often results in bending of the nanowires, in particular at the junctions of the segments. Magnetic collection of the nanowires results in significantly reduced bending but the remnant magnetized state of the nickel segments produces aggregated nanowires that reduce the efficiency of selective derivatization and leads to greater difficulty in subsequent imaging of single nanowires.

Figure 10:
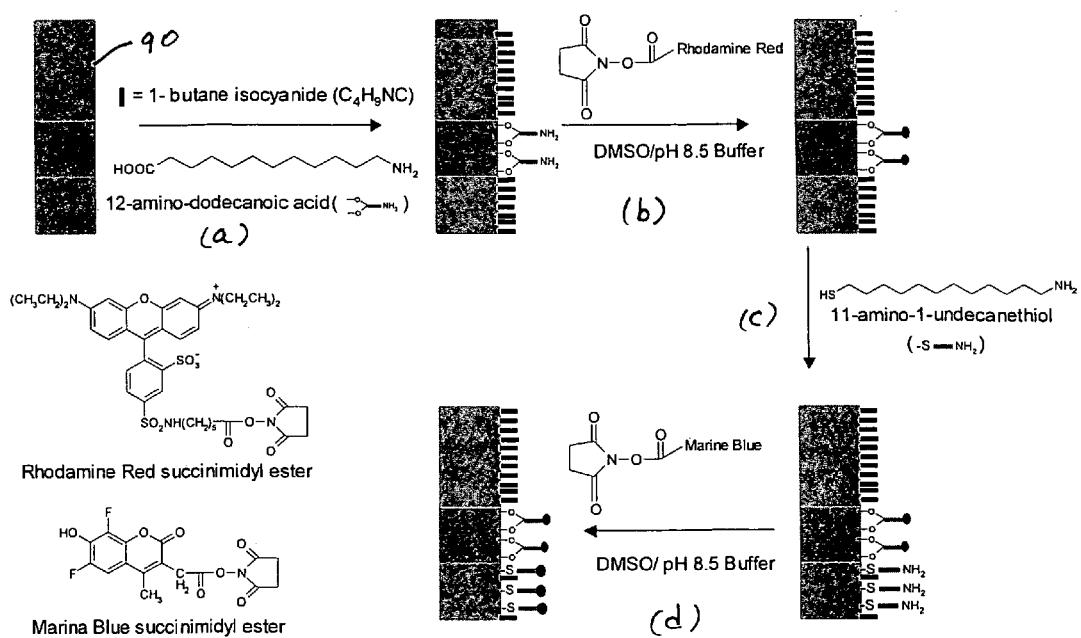
FIG. 10 schematically shows a general approach for selective derivatisation of Au/Ni/Pt nanowires.

FIG. 10 schematically illustrates the functionalization of the nanowires 90. In the first step of the functionalization (FIG. 10a), Au/Ni/Pt nanowires ($\approx 10^9$ mL$^{-1}$) are suspended in 2 ml of ethanol containing 2 mM 12-amino-dodecanoic acid (Aldrich) and 2 mM 1-butane isocyanide (BIC). The suspension is agitated using rotation for 24 hours. The nanowires 90 are then washed using repeat centrifugation and resuspension cycles using ethanol. The nanowires are then reacted with 3.84 mg Rhodamine Red succinimidyl ester (Molecular Probes) in 5 mL of a 50:50 mixture of pH 8.5 sodium tetraborate buffer and dimethylsulfoxide (DMSO) overnight under an argon blanket at room temperature (FIG. 10b). The succinimidyl ester reacts rapidly in the presence of primary amine groups producing a strong amide bond between the self-assembled monolayer molecules and the fluorophore. The nanowire suspension is then sonicated for 1 hour, followed by washes with DMSO, water and ethanol. For microscopic imaging, nanowires are spin coated onto a glass coverslip rotating at 2500 rpm for 15 secs.

FIGS. 11b and 11c show light microscope and fluorescence microscope images of the functionalized nanowires. Fluorescence from the rhodamine (Ex 570, Em 590) is predominantly localized to the Ni segment. Significantly weaker fluorescence is also observed on the Au and Pt sections. This is most probably due to physisorption between the hydrophobic rhodamine red flurophore and the hydrophobic BIC functionalised Au and Pt sections. Carboxylic acids have been reported to bind weakly to Au surfaces. The contrast between the weak fluorescence on the Au/Pt segments and the strong fluorescence on the Ni segment indicates that the BIC has preferentially bound to the Au/Pt surfaces significantly blocking carboxylic acid binding. Note that whilst the quenching of fluorescence molecules proximate to metal surfaces has been previously reported fluorophores bound to nanowires remain sufficiently detectable to identify selective functionalization.

Referring back to FIG. 10 the nanorods are next suspended in 2 ml of 2 mM 11-amino-1-undecanethiol (Dojindo) in ethanol and mixed using rotation for 24 hours (FIG. 10c). The nanowires are washed with ethanol using repeat centrifugation and resuspension cycles. The nanowires are then reacted with 3.67 mg Marina Blue succinimidyl ester (Molecular Probes) in 5 mL of a 50:50 mixture of pH 8.5 sodium tetraborate buffer and DMSO overnight under an argon blanket at room temperature (FIG. 10d). The nanowire suspension is then sonicated for 1 hour, followed by washes with DMSO, water and ethanol.

FIG. 11d-11g show light microscope and fluorescent microscope images of the tri-functionalized nanowires. FIG. 11e shows that fluorescence observed from the Marina Blue-1-undecanethiol (Ex 365, Em 460) is specifically from the gold segment. FIG. 11f shows that fluorescence from the rhodamine (Ex 570, Em 590) is still emanating from the Ni segment. Either very weak fluorescence (Ex 365, Em 460) or no fluorescence at all is observed from the longer Pt sections functionalised with BIC. This suggests that the carboxylic acid has retained its binding affinity to the Ni, whilst the thiol terminated molecules have displaced isonitril groups on the Au segment but not the Pt section. Surface engineering Au and Pt with BIC first followed by thiol displacement on the Au segment is preferential because of the reported ability of the BIC molecules to prop up the thiol terminated molecules in the upright orientation.

In control experiments, Au/Ni/Pt nanowires are functionalized with BIC and 12-amino-dodecanoic acid followed by treatment with Rhodamine Red succinimidyl ester. When the wires are then exposed to 1-decanethiol, fluorescence is observed only on Ni segments. Similarly, when the nanowires are functionalized with BIC and palmitic acid, followed by exposure to 11-amino-1-undecanethiol, subsequent treatment with Marina blue succinimidyl ester results in fluorescence predominantly observed on the Au sections.

In summary, this example demonstrates selective derivatization of three component Au/Ni/Pt nanowires using metal specific surface chemistries. The ability to direct unique fluorescent, biological or chemical molecules to individual segments in three or more component nanowires has potential for further advances in gene/drug delivery, chemical sensing and self-assembly.

It is understood that the above-described embodiments are illustrative of only a few of the many possible specific embodiments, which can represent applications of the invention. Numerous and varied other arrangements can be made by those skilled in the art without departing from the spirit and scope of the invention.

Appendix A

Methods and Materials of Example 1

Functionalization of Nanorods

DNA binding. 150 µL of 0.1 M AEDP (Pierce) solution was added to 200 µL aliquots of nanorods (~1 ×10$^6$) suspended in distilled water. Following incubation for 24 h and washing, 2 µg of plasmid was added to each aliquot of nanorods, (pH 5.7) and incubated at 4° C. for 24 h. After washing, 2 µL of a 2M CaCl$_2$ solution was added to each aliquot and then incubated for 24 h at 4° C. For fluorescent staining of plasmids, nanorods were incubated in 100 µL of 1×Hoechst 33258.

Transferrin building. 5 mg of rhodamine-conjugated transferrin (Molecular probes) in PBS with 5 mM EDTA was reacted with 120 µL of 5 mg mL$^{-1}$ iminothiolane (Pierce) for 30 minutes at room temperature. The protein was purified by dialysis at 4° C. 20 µof 5 mg mL−1 rhodamine-transferrin-SH was added to each aliquot of nanorods and incubated for 24 h at 4° C.

Transfection experiments. HEK293 cells (ATCC) were cultured in T75 flasks in DMEM with 10% FCS and ABAM. All cell culture and Lipofectamine reagents were purchased from Gibco BRL, Rockville, Md. The srum-containing media was replaced every 3 days and split 1:3 at pre-confluence. The plasmids were a gift from Dr. Carl Wheeler, Vical Incorporated. HEK293 cells were seeded onto 24-well plates (3×10$^5$ cells/well) for transfection using luciferase-plasmid, 12-well plates (8×10$^5$ cells/well) for tranfecting using GFP-plasmid and 6-well plates (2×10$^6$ cells/well) for SEM and TEM. Each well (24-well) was transfected in 0.5 mL reduced-serum Opti-MEM media. Selected wells were incubated with Opti-MEM containing 100 µM chloroquine. Lipfectamine: DNA complexes at a ratio of 4:1 using 8 µg Lipofectamine in 40 µL Opti-MEM and 2 µg DNA in 40 µL Opti-MEM was added to control wells. 40 µL of the nanorods/DNA suspension was added per well. After 4 hrs, transfection media was removed and cells washed. After 2 days of further incubation in serum-containing media, wells were washed with phosphate buffered saline (PBS) and imaged live. For confocal microscopy, chamber slides (Thomas Scientific Co. Swedesboro, N.J.) were coated with 50 µg/mL collagen in 0.1 M acetic acid, washed with PBS and seeded with 5×10$^4$ cells. After 24 hrs, transfection was undertaken with GFP plasmid. For acidic organelle staining, HEK293 cells with nanorods were incubated with 75 nM Lysotracker Green (Molecular Probes) at 37° C. for 1 hr in Opti-MEM media. Live HEK293 cells were viewed under a laser scanning confocal microscope (Carl Zeiss Inc. USA). Transfection with the luciferase-plasmid followed the same protocol for GFP-plasmid with relative light units (RLU) measured using a luminometer (EG&G Berthold MiniLumat) and normalized to protein content using the BCA protein assay (Biorad). For SEM and TEM studies on internalization, cells were fixed with 2% glutaraldehyde/2% paraformaldehyde inPBS at selected time-points. After washing with PBS, cells were dehydrated with graded ethanol and coated with 2% osmium tetroxide (Aldrich). SEM samples were gold/platinum coated. TEM samples were sectioned in epoxy resin by microtome and developed using 2% uranyl acetate and 0.04% lead citrate.

Appendix B

Methods and Materials of Example 2

Preparation of 200 nm Dual Component Au/Ni Nanowires

Nanowires were fabricated by electrodeposition into an Al$_2$O$_3$ template (Anodisc, Whatman) with a nominal pore diameter of 100 nm. An evaporated silver film on one side of the template served as the working electrode in a three-electrode configuration. A thin layer of silver was first electrodeposited from 50 mM KAg(CN)$_2$ and 0.25 M Na$_2$CO$_3$ buffered to pH 13 at a potential of −1.0 V (Ag/AgCl) in order to ensure easy release of the nanowires from the template. The Au segments were deposited from a commercial gold plating solution (Technic) at a potential of −1.0 V (Ag/AgCl) and the Ni segments were deposited from a solution of 20 g L$^{-1}$ NiCl$_2$ .6H$_2$O, 515 g L$^{-1}$ Ni (H$_2$NSO$_3$)$_2$ .4H$_2$O), 20 g L$^{-1}$ H$_3$B0$_3$ buffered to pH 3.4 at a potential of −1.0 V (Ag/AgCl). The silver layers were dissolved in 70 vol. % nitric acid and the alumina template was then dissolved in 2 M KOH. The nanowires were washed repeatedly using 2 M KOH, de-ionized water, and ethanol.

Functionalization of Au/Ni Nanorods

DNA binding: A 150 µL of 0.1 M AEDP (Pierce) solution was added to 200 µL aliquots of nanorods(−1×10$^6$) suspended in distilled water. Following incubation for 24 h and washing, 2 µg of plasmid was added to each aliquot of nanorods, (pH 5.7) and incubated at 4° C. for 24 h. After washing, 2 µl of a 2M CaCl$_2$ solution was added to each aliquot and then incubated for 24 h at 4° C.

Ovalbumin binding: Five mg of ovalbumin in PBS with 5 mM EDTA was reacted with 120 µl of 5 mg ml$^{-1}$ iminothiolane (Pierce) for 30 minutes at room temperature. The protein was purified by dialysis at 4° C. Twenty µl of 5 mg ml$^{-1}$ ovalbumin-SH was added to each aliquot of nanorods and incubated for 24 h at 4° C.

Immunization Experiments

We purchased 6-to8-week-old male C57BL/6 mice from the National Cancer Institute (Frederick, Md.) and kept them in the oncology animal facility of the John Hopkins Hospital (Baltimore, Md.). All animal procedures were performed according to approved protocols and in accordance with recommendations for the proper use and care of laboratory animals.

Gene gun particle-mediated DNA vaccination was performed using a helium-driven gene gun (Bio-Rad, Hercules, Calif.) according to the protocol provided by the manufacturer. Briefly, DNA-coated gold particles were prepared by combing in 25 mg of 1.6 µm of gold microcarriers (Bio-Rad, Hercules, Calif.) and 100 µl of 0.05 M spermidine (Sigma, St. Louis, Mo.). Plasmid DNA (50 µg) and 1.0 M CaCl$_2$ (100 µl) were added sequentially to the microcarriers while mixing by vortex. Antigen-coated gold particles were prepared using the same protocol with the exception of the addition of CaCl$_2$. The mixture was allowed to precipitate at room temperature for 10 min. The microcarrier/DNA suspension was then centrifugated (10,000 rpm for 5 s) and washed three times in a fresh absolute ethanol before resuspending in 3 ml of polyvinylpyrrolidone (0.1 mg/ml; Bio-Rad, Hercules, Calif.) in absolute ethanol. At this stage, Nanowire-pcDNA$_3$-OVA7 formulations and Nanowire-Ovalbumin formulations at the appropnate concentrations were also resuspended in 3 ml of polyvinylpyrrolidone (0.1 mg/ml; Bio-Rad, Hercules, Calif.) in absolute ethanol. The solutions were then loaded into tubing and allowed to settle for 4 min. The ethanol was gently removed, and the microcarrier/DNA suspension was evenly attached to the inside surface of the tubing by rotating the tube. The tube was then dried by 0.4 liters/min of flowing nitrogen gas. The dried tubing coated with microcarrier/DNA was then cut to 0.5 inch cartridges and stored in a capped dry bottle at 4° C. As a result, each cartridge contained 1 µg of plasmid DNA and 0.5 mg of gold particles or nanowires. The DNA-coated gold particles (1 µg of DNA/bullet), the antigen coated-gold particles, the DNA-coated nanowires and the antigen coated nanowires (each 1 µg of DNA or antigen/bullet) were delivered to the shaved abdominal region of the mice using a helium-driven gene gun (Bio-Rad, Hercules, Calif.) with a discharge pressure of 400 p.s.i. Mice were given a booster 2 weeks after the initial shots.

Anti-OVA7 ELISA

The anti-OVA7 antibodies in the sera were determined by a direct ELISA. A 9-microwell plate was coated with 100 µl of 10 µg/ml ovalbumin antigen and incubated at 4° C. overnight. The wells were then blocked with PBS containing 20% fetal bovine serum. Sera were prepared from the mice on day 21 after the initial vaccination, serially diluted in PBS, added to the ELISA wells, and incubated on 37° C. for 2 h. After washing with PBS containing 0.05% Tween-20, the plate was incubated with 1/2000 dilution of a peroxidase-conjugated rabbit antimouse IgG antibody (Zymed, San Francisco, Calif.) at room temperature for 1 h. The plate was washed six times, developed with 1-Step Turbo TMB-ELISA (Pierce, Rockford, Ill.), and stopped with 1 M H$_2$SO$_4$. The ELISA plate was read with a standard ELISA reader at 450 nm.

Intracytoplasmic Cytokine Staining and Flow Cytometry Analysis

Splenocytes from the vaccinated mice were incubated with ovalbumin. The ovalbumin was added at a concentration of 2 µg/ml for 20 h. To detect ovalbumin-specific CD8+ T-cell precursors, CD8+ CTL epitopes were used. Golgistop (PharMingen, San Diego, Calif.) was added 6 h before harvesting the cells from the culture. Cells were then washed once in FACScan buffer and stained with phycoerythrin-conjugated monoclonal rat antimouse CD8 antibody (PharMingen, San Diego, Calif.). Cells were subjected to intracellular cytokine staining using the Cytofix/Cytoperm kit according to the manufacturer's instructions (PharMingen). FITC-conjugated anti-IFN-and the immunoglobulin isotype control antibody (rat IgGl) were all purchased from PharMingen. Analysis was done on a Becton Dickinson FACScan with CELLQuest software (Becton Dickinson Immunocytometry System, Mountain View, Calif.).

What is claimed is:

1. A method of delivering active biological molecules to cells comprising the steps of:
   providing a nanoscale structure comprising a plurality of discrete regions of respectively different materials;
   binding a biological molecule to a first discrete region of the nanoscale structure and binding a second molecule different from the biological molecule to a second discrete region of material different from that of the first region; and
   delivering the nanoscale structure with the bound molecules to cells.

2. The method of claim 1 wherein the nanoscale structure comprises a plurality of discrete regions of respectively different materials.

3. The method of claim 1 wherein the nanoscale structure is selected from the group consisting of nanotubes, nanoscale bars, nanodisks, nanoscale ovals, nanoscale parallelpipeds and nanoparticles of regular or irregular shape.

4. The method of claim 1 wherein the nanoscale structure is provided by electrodepositing successively different layers into a nanoporous matrix and removing the matrix.

5. The method of claim 1 wherein at least one of the molecules comprises a sequence of DNA.

6. The method of claim 5 wherein the DNA comprises a sequence encoding a protein.

7. The method of claim 5 wherein the DNA comprises a sequence encoding an antigen.

8. The method of claim 1 wherein at least one of the molecules comprises a protein.

9. The method of claim 1 wherein at least one of the molecules is one that activates a cell receptor.

10. The method of claim 1 wherein at least one of the molecules comprises transferrin.

11. The method of claim 1 wherein at least one of the molecules comprises a genetic material and at least another of the molecules activates a cell receptor.

12. The method of claim 1 wherein at least one of the molecules comprises a sequence of DNA encoding an antigen and at least another of the molecules comprises an adjuvant that enhances immune response to the antigen.

13. The method of claim 1 wherein at least one of the molecules comprises an antigen and at least another of the molecules comprises an adjuvant that enhances immune response to the antigen.

14. The method of claim 1 wherein at least one of the molecules comprises an antigen and at least another of the molecules comprises a sequence of DNA encoding the antigen.

15. The method of claim 1 wherein at least one of the molecules comprises a first antigen and at least another of the molecules comprises a second antigen.

16. The method of claim 1 wherein the nanoscale structure comprises at least three discrete regions of respectively different materials.

17. A method of delivering active biological molecules to cells comprising the steps of:
   providing a nanoscale structure comprising a plurality of discrete regions of respectively different materials, the discrete regions having bound thereto respectively different molecules, and
   delivering the nanoscale structure with the bound molecules to cells.

18. The method of claim 17 wherein the nanoscale structure is delivered to cells by injecting the structure into the cells or adjacent tissues.

19. The method of claim 17 wherein at least one of the molecules comprises a molecule that activates a cell receptor permitting entry into the cell and the nanoscale structure is delivered to cells by injecting the structure adjacent a cell.

20. The method of claim 1 wherein at least one of the molecules comprises compacted DNA.

* * * * *